(12) United States Patent
Takkellapati et al.

(10) Patent No.: US 8,067,580 B2
(45) Date of Patent: *Nov. 29, 2011

(54) ISOLATION OF DNA, RNA AND PROTEIN FROM A SINGLE SAMPLE

(75) Inventors: Sudhakar Rao Takkellapati, Walpole, MA (US); Joseph W. Farchaus, Bloomsbury, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/863,775

(22) PCT Filed: Feb. 5, 2009

(86) PCT No.: PCT/US2009/033137
§ 371 (c)(1), (2), (4) Date: Jul. 21, 2010

(87) PCT Pub. No.: WO2009/100172
PCT Pub. Date: Aug. 13, 2009

(65) Prior Publication Data
US 2010/0292446 A1    Nov. 18, 2010

Related U.S. Application Data

(60) Provisional application No. 61/026,742, filed on Feb. 7, 2008.

(51) Int. Cl.
*C07H 21/00* (2006.01)
(52) U.S. Cl. .................. 536/25.4; 536/25.41; 536/25.42
(58) Field of Classification Search .................. None
See application file for complete search history.

(56) References Cited

U.S. PATENT DOCUMENTS

| | | | |
|---|---|---|---|
| 5,561,064 A | 10/1996 | Marquet et al. | |
| 5,707,812 A | 1/1998 | Horn et al. | |
| 5,801,237 A | 9/1998 | Johansson | |
| 5,856,192 A | 1/1999 | Bloch | |
| 5,866,428 A | 2/1999 | Kim et al. | |
| 5,990,301 A | 11/1999 | Colpan et al. | |
| 6,090,288 A | 7/2000 | Berglund et al. | |
| 6,310,199 B1 | 10/2001 | Smith et al. | |
| 6,410,274 B1 | 6/2002 | Bhikhabhai | |
| 7,655,792 B2 | 2/2010 | Takkellapati et al. | |
| 7,655,793 B2 | 2/2010 | Herzer et al. | |
| 7,655,794 B2 * | 2/2010 | Takkellapati et al. ........ | 536/25.4 |
| 2005/0019814 A1 | 1/2005 | Laugharn, Jr. et al. | |
| 2005/0079535 A1 | 4/2005 | Kirchgesser et al. | |
| 2005/0130151 A1 | 6/2005 | Warren et al. | |
| 2006/0051771 A1 | 3/2006 | Murphy et al. | |
| 2006/0182657 A1 | 8/2006 | Pathirana et al. | |
| 2007/0292437 A1 | 12/2007 | Jackson | |

FOREIGN PATENT DOCUMENTS

| | | |
|---|---|---|
| EP | 0 616 639 | 11/1998 |
| EP | 0 992 583 | 3/2003 |
| EP | 1 125 943 | 10/2004 |
| WO | WO 03/062462 | 7/2003 |

OTHER PUBLICATIONS

Dimino, M., et al., Journal of Chromatography B, (2007), 856(1-2):353-357.

Tseng, W.-C., et al., Journal of Chromatography B, (2003), 791:263-272.

* cited by examiner

*Primary Examiner* — Lawrence E Crane

(57) ABSTRACT

The invention provides a method for the separation and purification of two or three cellular components selected from genomic DNA, RNA and proteins from a single biological sample. The method comprises generating an aqueous solution containing the cellular components by lysing cells with a lysis solution; contacting the aqueous solution with an ion exchanger for genomic DNA and RNA to bind to the ion exchanger; collecting the flow-through which contains unbound proteins; eluting RNA from the ion exchanger; and eluting DNA from the ion exchanger. For the purification of any two of the cellular components, one of the components is not collected. The invention also provides reagent kits for carrying out the methods.

14 Claims, 2 Drawing Sheets

ISOLATION OF DNA, RNA AND PROTEIN FROM A SINGLE SAMPLE

CROSS-REFERENCE TO RELATED APPLICATIONS

This application is a filing under 35 U.S.C. §371 and claims priority to international patent application number PCT/US2009/033137 filed Feb. 5, 2009, published on Aug. 13, 2009, as WO 2009/100172, and claims priority to U.S. provisional patent application No. 61/026,742 filed Feb. 7, 2008; the disclosure of which is incorporated herein by reference in its entirety.

FIELD OF THE INVENTION

This invention relates generally to methods for the separation and isolation of genomic DNA, RNA and proteins from a biological sample. In particular, the invention relates to the simultaneous isolation of two or more of DNA, RNA and proteins from a single biological sample, using an ion exchange chromatography media in combination with buffers specific for the separation of each of the components.

BACKGROUND OF THE INVENTION

The last three decades has seen considerable effort in the development of improved methods for the isolation and purification of nucleic acids and proteins from biological sources. This has been due mainly to the increasing applications of these materials in the medical and biological sciences. Although it is advantageous in many occasions to isolate nucleic acids and proteins from the same sample, effective methods have been lacking.

Currently the most used protocol for simultaneous isolation of genomic DNA, RNA and proteins from different types of samples is a solution phase based method which utilizes TRI reagent (TRIzol; BioTechniques, 35, 450-456 (2003)). This process is based on organic/aqueous extractions and it involves the use of toxic chemicals, which include chloroform, bromochloropropane, phenol and guanidine isothiocyanate. The other drawback of this solution phase method is the difficulty in separation of the layers. If the layers are not completely separated there will be considerable amount of cross contamination.

Recently Norgen Biotek launched a silicon carbide bead based chromatography product for the isolation of DNA, RNA and protein (RNA/DNA/Protein Purification Kit). Macherey-Nagel offers a product for isolation of RNA and Protein (NUCLEOSPIN® RNA/Protein Kit). This product can be combined with a buffer set commercialized by Macherey-Nagel to accomplish the isolation of all three components. All these products are silica based technologies.

Another method for the simultaneous isolation of genomic DNA, RNA and proteins is recently disclosed in PCT application WO 03/062462 by Dynal Biotech. In this patent application, the authors propose using distinct solid supports for the isolation of DNA, mRNA and protein. The specific solid supports are dT or dU oligo derivatized support, carboxylic acid derivatized support, dynabeads derivatized with amine and magnetic particles. In summary they use different types of resins for the isolation of three different components from one sample. This is done by a stepwise addition of a specific solid support to the lysate, removal of this support and then the addition of a second support to the lysate to isolate the second component and so on. Here DNA is isolated by complexation mechanism and mRNA is isolated by affinity methods.

Currently several procedures are available for the chromatographic purification of DNA (genomic and plasmid) and RNA, for example, by employing silica based membrane purification, size exclusion chromatography, reversed phase chromatography, gel filtration, magnetic bead based purification, or ion-exchange chromatography. Ion exchange chromatography is one of the most commonly used separation and purification methods and has been used for purification of plasmid DNA, genomic DNA and RNA. See for example, U.S. Pat. No. 6,410,274 (Bhikhabhai), U.S. Pat. No. 6,310,199 (Smith et al), U.S. Pat. No. 6,090,288 (Berlund et al), U.S. Pat. No. 5,990,301 (Colpan et al), U.S. Pat. No. 5,856,192, U.S. Pat. No. 5,866,428 (Bloch), U.S. Pat. No. 5,801,237 (Johansson), EP 1125943 B1 (Macherey-Nagel GmbH & Co), EP 992583 B1, EP 616639 (Qiagen), U.S. Pat. No. 5,707,812 and U.S. Pat. No. 5,561,064 (Vical Inc.).

While anion exchange chromatographic procedures for the purification of nucleic acids have been extensively referenced, one of the shortcomings of current protocols is the impaired recovery of nucleic acid during the elution step. Addition of organic agents such as polyols and alcohols during adsorption and desorption has been shown to improve selectivity and recovery during anion exchange purification of DNA (Tseng, W. C. et al, J. Chromatogr. B Analyt. Technol. Biomed. Life Sci., (2003), 791(1-2), 263-72). Recently, improvements have been made to the elution buffer that specifically address the recovery issues often seen during DNA desorption from anion exchange resins (See U.S. Pat. Nos. 7,655,792 and 7,655,793). These improved methods whether by an increase in the pH of the elution solution, or by the inclusion of specific salt compositions, greatly increase the recovery rate of bound nucleic acids from an anion exchange column.

There remains a need for improved methods for the simultaneous isolation of genomic DNA, RNA and proteins from a single sample.

BRIEF DESCRIPTION OF THE INVENTION

The invention provides methods for the simultaneous isolation of genomic DNA, RNA and proteins from a single sample, using an ion exchange chromatography media in combination with buffers specific for the separation of each of the components.

Thus, in a first aspect the present invention provides a method for the separation and/or purification of two or three cellular components selected from genomic DNA, RNA and proteins. The method comprises (a) generating an aqueous solution containing the cellular components by lysing cells with a lysis solution; (b) contacting the aqueous solution with an ion exchanger under conditions such that genomic DNA and RNA bind to the ion exchanger; (c) collecting the flow-through which contains unbound proteins; (d) eluting RNA from the ion exchanger with an RNA elution solution; and (e) eluting DNA from the ion exchanger with an DNA elution solution. For the purification of any two of the cellular components, one of steps (c) through (e) can be modified or omitted such that: for the purification of genomic DNA and RNA alone, the flow-through in step (c) is not collected; for the purification of genomic DNA and proteins alone, RNA eluted from step (d) is not collected; and for the purification of RNA and proteins alone, step e) is omitted.

In certain embodiments according to the first aspect of the invention, the proteins collected from step (c) are further purified. In other embodiments, the genomic DNA or RNA is further purified using a desalting device.

In a second aspect, the invention provides a kit for the separation and/or purification of two or three of the cellular components: genomic DNA, RNA and proteins from a single biological sample. The kit comprises (a) a lysis solution for generating an aqueous solution containing the genomic DNA, RNA and proteins by lysing the biological sample; (b) an anion exchanger for binding the genomic DNA and RNA; (c) an RNA elution solution for eluting the RNA from said anion exchanger; (d) a genomic DNA elution solution for eluting the genomic DNA from said anion exchanger; (e) desalting means for desalting each of the eluted genomic DNA and RNA, respectively; and (f) means for purifying proteins from the flow through after genomic DNA and RNA bound to the anion exchanger. The RNA elution solution has a lower salt concentration than the DNA elution solution, and the RNA elution solution has a higher salt concentration than the lysis solution.

In certain embodiments according to the second aspect of the invention, not all of the reagents are essential. Thus, when one of the cellular components is not of particular interest, reagents for isolating that component may be optional. For example, when isolating genomic DNA is not necessary, DNA elution solution need not be present in the kit.

Other features and advantages of the invention will be apparent from the following description of the preferred embodiments, and from the claims.

DETAILED DESCRIPTION OF THE PREFERRED EMBODIMENTS

Figure 1:
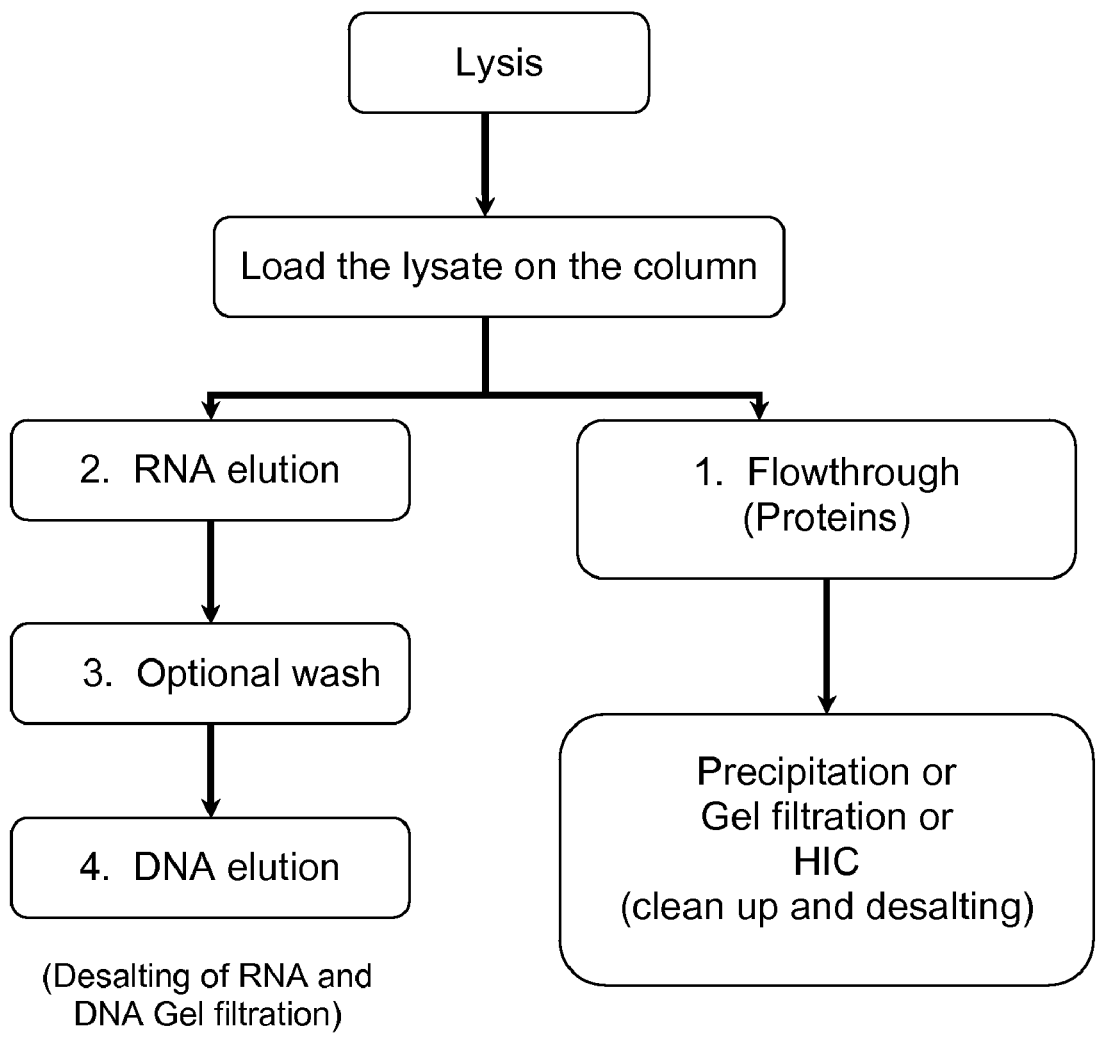
FIG. 1 shows a work flow for the isolation of genomic DNA, RNA and protein from a single sample.

Recently, improvements have been made to the elution buffer which greatly increases the recovery rate of nucleic acid desorption from anion exchange resins (See U.S. Pat. Nos. 7,655,792 and 7,655,793). These methods either by an increase in the pH of the elution solution, or by the inclusion of specific salt compositions, greatly increase the recovery rate of bound nucleic acids from an anion exchange column. One example of an additive is guanidine or a guanidine-like derivative. Another example is a potassium carbonate. The addition of either additive to the elution solution has been shown to improve recovery of nucleic acids from anion exchange resins from 20-50% to 70-95%.

Here the improved method has been further developed for the simultaneous isolation of DNA, RNA and protein from a single sample. Thus, in a first aspect the present invention provides a method for the separation and/or purification of two or three cellular components selected from genomic DNA, RNA and proteins. The method comprises (a) generating an aqueous solution containing the cellular components by lysing cells with a lysis solution; (b) contacting the aqueous solution with an ion exchanger under conditions such that genomic DNA and RNA bind to the ion exchanger; (c) collecting the flow-through which contains unbound proteins; (d) eluting RNA from the ion exchanger with an RNA elution solution; and (e) eluting DNA from the ion exchanger with an DNA elution solution. Optionally, a wash step is included after step (d), to remove any trace amount of RNA from the ion exchanger, prior to elution of DNA.

For the purification of any two of the three cellular components, one of steps (c) through (e) could be modified. For the purification of genomic DNA and RNA alone, the flow-through collected in step (c) is discarded. For the purification of genomic DNA and proteins alone, RNA eluted from step (d) need not be collected. For the purification of RNA and proteins alone, step (e) is omitted.

While the cellular components are effectively separated by the method, additional steps are sometimes necessary to further purify the separated cellular components. As an example, proteins collected in the flow-through of step (c) can be further purified using conventional methods. It is well known that proteins can be further purified by precipitation, gel filtration, affinity chromatography or hydrophobic interaction chromatography (HIC). Similarly, genomic DNA eluted from step (e) can be further purified by a desalting step. RNA eluted from step (d) can also be further purified by a desalting step. DNA and RNA desalting can be accomplished using a variety of methods, such as an NAP™-10 or NAP™-25 column (GE Healthcare) or any other commercially available membrane based desalting devices. Small amount of cross-contamination of DNA and RNA in the reciprocal sample can be eliminated by optimized elution buffers, while trace amount of cross contamination in the other sample can be removed by treating with enzymes such as RNase A or a DNase.

The method of the invention is realized by the finding that nucleic acids bind to the chromatography resin at a low salt level, while RNA and genomic DNA can be eluted at increased salt level, although at certain intermediate salt concentrations only RNA elutes from the column, and DNA continues to bind to the column. Thus in one example, the lysed sample will be loaded on an ion-exchange resin column with a salt concentration of about 200 to 500 mM. During the loading step all the proteins will be eluted in the flow-through. Both genomic DNA and RNA will bind to the column RNA can then be eluted using 625-750 mM salt strength buffer. At this point a wash step may be incorporated to eliminate any trace amount of RNA left on the column which might co-elute with DNA. Finally DNA is eluted using a buffer with higher salt concentration.

The optimal buffer for eluting DNA from the ion-exchange column has a pH of between about pH 9 and about pH 13, preferably between about pH 10 and about pH 12, most preferably between about pH 10.5 and about pH 11.6. As an example, a suitable buffer includes potassium carbonate, at a concentration of about 0.1M-2 Molar.

The process according to the present invention is particularly suitable for the preparation and/or purification of genomic DNA, RNA and protein derived from complex mixtures of components of cellular and tissue samples from any recognised source, including normal and transformed cells, with respect to species (e.g. human, rodent, simian), tissue source (e.g. brain, liver, lung, heart, kidney skin, muscle) and cell type (e.g. epithelial, endothelial, blood). Furthermore, the present method is suitable for the preparation and/or purification of genomic DNA having an average fragment size of from about 0.1 kilo-bases to about 200 kilo-bases.

Nucleic acids display strong binding affinities to anion exchange resins. Anion exchange resins suitable for use with methods of the present invention include both strong anion exchangers and weak anion exchangers, wherein the anion exchange resin suitably comprises a support carrier to which charged or chargeable groups have been attached. The ion exchange resin may take the form of a bead, a membrane or a surface. Examples of strong anion exchange resins include Q-SEPHAROSE™ fast flow resin, Q-SEPHAROSE™ XL and CAPTOQ™. Examples of weak ion exchange resins include ANX-SEPHAROSE™ fast flow resin, DEAE SEPHAROSE™ and DEAE SEPHADEX™ A25 resin (GE Healthcare).

Preferably, the ion-exchange chromatography is accomplished utilizing gravity and spin based methods. Alternatively, positive pressure and vacuum based methodologies can also be employed. Positive pressure and vacuum based methodologies are preferred for an automated sample preparation system or high throughput processing.

In a second aspect, the invention provides a kit for the separation and/or purification of genomic DNA, RNA and proteins from a single biological sample. In a particular embodiment, the kit is suitable for the separation and/or purification of all three components. This kit comprises a lysis solution for generating an aqueous solution containing the genomic DNA, RNA and proteins by lysing the biological sample; an anion exchanger for binding the genomic DNA and RNA; an RNA elution solution for eluting the RNA from the anion exchanger; and a genomic DNA elution solution for eluting the genomic DNA. Preferably, the anion exchanger is ANX-SEPHAROSE™ FF, Q-SEPHAROSE™ FF, DEAE SEPHAROSE™ or DEAE SEPHADEX™. Preferably, the RNA elution solution has a lower salt concentration than the DNA elution solution, and has a higher salt concentration than the lysis solution. Suitably there is present in the DNA elution solution an additive such that the pH of the elution solution is between about pH 9 and about pH 13. Preferably the DNA elution solution includes potassium carbonate at a concentration of about 0.1M-2 Molar. Optionally, the kit also includes separate desalting means for desalting each of the eluted genomic DNA and RNA, respectfully; and means for purifying proteins from the flow through after genomic DNA and RNA binds to the anion exchanger.

In another embodiment, the invention provides a kit for the separation and/or purification of genomic DNA and RNA from a single biological sample, which kit comprises a lysis solution for generating an aqueous solution containing the genomic DNA and RNA by lysing said biological sample; an anion exchanger for binding the genomic DNA and RNA; an RNA elution solution for eluting the RNA from the anion exchanger; and a genomic DNA elution solution for eluting the genomic DNA from the anion exchanger. Optionally, the kit further includes desalting means for desalting each of the eluted genomic DNA and RNA, respectfully. Preferably, the RNA elution solution has a lower salt concentration than the DNA elution solution, and a higher salt concentration than the lysis solution.

In yet another embodiment, the invention provides a kit for the separation and/or purification of genomic DNA and proteins from a single biological sample, which kit comprises a lysis solution for generating an aqueous solution containing the genomic DNA and proteins by lysing said biological sample; an anion exchanger for binding the genomic DNA; a wash solution for washing off RNA bound to the anion exchanger; a genomic DNA elution solution for eluting the genomic DNA from the anion exchanger. Optionally, the kit further includes a desalting means for desalting the eluted genomic DNA; and a means for purifying proteins from the flow through after genomic DNA bound to the anion exchanger. Preferably, the RNA wash solution has a lower salt concentration than the DNA elution solution, and a higher salt concentration than the lysis solution.

In still another embodiment, the invention provides a kit for the separation and/or purification of RNA and proteins from a single biological sample, which kit comprises a lysis solution for generating an aqueous solution containing the RNA and proteins by lysing the biological sample; an anion exchanger for binding the RNA; an RNA elution solution for eluting the RNA from the anion exchanger. Optionally, the kit further includes a desalting means for desalting the eluted RNA; and a means for purifying proteins from the flow through after RNA bound to the anion exchanger. Preferably, the RNA elution solution has a higher salt concentration than the lysis solution.

EXAMPLES

The following examples serve to illustrate the genomic DNA, RNA and protein purification processes according to embodiments of the present invention and are not intended to be limiting.

(A) Protocol for the Isolation of Genomic DNA, RNA and Protein from Tissue Samples The tissue sample is prepared by the following steps. It is critical to have a completely homogenized sample to obtain good yield of genomic DNA, RNA and proteins from the purification process.

(a) Homogenization and Lysis

1. Weigh approximately 100 mg of tissue by slicing into very fine pieces.
2. Wash the tissue with 1×PBS buffer. Add 1 ml of 1×PBS buffer, vortex and centrifuge at 1000 RPM for 1 min. Discard the washing and remove any traces of buffer left in the tube using a pipette.
3. Add 0.5 ml of 1×PBS buffer and homogenize the sample by handheld homogenizer.
4. Add 0.5 ml of Lysis Solution (20 mM Tris-HCl, 20 mM EDTA, 100 mM sodium chloride and 1% SDS) to the homogenized sample (PBS and lysis solution in 1:1 ratio) and vortex at the highest possible speed for 20-30 sec.
5. Incubate at room temperature for 15 min
6. Dilute the crude lysate with 4 ml of Nuclease-free water and 5 ml of Loading Solution (500 mM sodium chloride, 50 mM Tris and 1 mM EDTA) and centrifuge at 5000×g for 15 min to pellet particulates.

(b) Separation of Proteins, Genomic DNA and RNA

1. Remove the cap from the top of an ion-exchange purification column (approximately 1.5 ml of ion-exchange resin in a plastic tube, packed using an automated process on an instrument). Discard the solution by decanting. Cut the closed end of the column at the notch and place the column in 50 ml centrifuge tubes using a column adaptor.
2. Transfer the lysate generated from the lysis step (6) above to the column and allow it to flow completely through the resin by gravity.
3. Collect the flow-through which contains the protein.
4. Apply 5 ml of Loading Solution to the column and collect the flow-through which contains proteins.
5. When all the Loading solution passes through the resin, place the column in a fresh 50 ml centrifuge tube.
6. Add 9 ml of RNA Elution Solution (750 mM sodium chloride, 50 mM Tris and 1 mM EDTA) to the column and collect the RNA product in the eluate.
7. Optionally add 4 ml of a Wash Solution (same composition as the RNA Elution Solution) to the column to wash off any trace amount of RNA not eluted in step above. The eluate may be collected for maximized RNA yield.
8. Add 3 ml of DNA Elution Solution (1M sodium chloride+ 0.5 M potassium carbonate) to the column and collect the DNA product in the eluate.

(c) Further Purification of Proteins, Genomic DNA and RNA
(i) Protein Purification The protein collected in the flow-through can be further purified by conventional methods such as precipitation, gel filtration or HIC method.

(ii) Genomic DNA and RNA Purification

Genomic DNA and RNA can be further purified by a quick gravity flow column such as a SEPHADEX™ G-25 column, for example a NAP™-10 or NAP™-25 column (GE Healthcare), following these steps:

1. Remove the cap of a desalting column and discard the solution. Cut the closed end of the column at notch and place the column in a centrifuge tube using the adaptor.
2. Equilibrate the column by applying 25 mL of 1×TE buffer. This can be accomplished by using LabMate PD-10 buffer reservoir.
3. Transfer the eluate (e.g., 2.5 ml for a NAP™-25 column) to the desalting column and allow it to flow by gravity.
4. When the solution completely enters the gel bed, place the column in fresh 50 ml centrifuge tube.
5. Add 1×TE buffer (e.g., 3.5 ml for a NAP™-25 column) to each column and collect the eluate containing genomic DNA or RNA. The desalted samples are now ready for quantification and downstream applications (d) Quantification of the Purified Genomic DNA and RNA Samples Quantification of the purified genomic DNA and RNA samples were achieved with a UV spectrophotometer, using 1×TE Buffer pH8.0 as the blank and 1 cm path length cuvettes. Readings of three samples were taken at A260, A280 and A320. Yield of DNA ($\mu$g)=A260×50 $\mu$g×Eluted sample volume (3.5 ml). Yield of RNA ($\mu$g)=A260×40 $\mu$g×Eluted sample volume (3.5 ml).

(B) Isolation of Genomic DNA, RNA and Protein from Tissue Samples

Approximately 100 mg of rat liver was homogenized and lysed according to the procedure described in the protocols section. The crude lysate was diluted with loading solution and the particulates removed by centrifugation. The supernatant was transferred to the ion-exchange purification column (i.e., ANX SEPHAROSE™ Fast Flow (high sub)). The columns were pre-packed using a salt solution having similar strength as the sample loading solution, with suitable antimicrobial agent (e.g. lower alcohol or ketone). This eliminates the need for column equilibration prior to loading of the sample in loading solution for binding of the nucleic acid.

The components (i.e., protein, genomic DNA and RNA) were separated according to the protocol above. Proteins were collected in the flow-though, RNA and genomic DNA were collected using elution buffer specifically made for RNA or genomic DNA as disclosed above. The genomic DNA and RNA thus obtained was desalted using NAPT™-25 column The purity and integrity of the products were assessed by UV spectrophotometry and by gel analysis.

Figure 2:
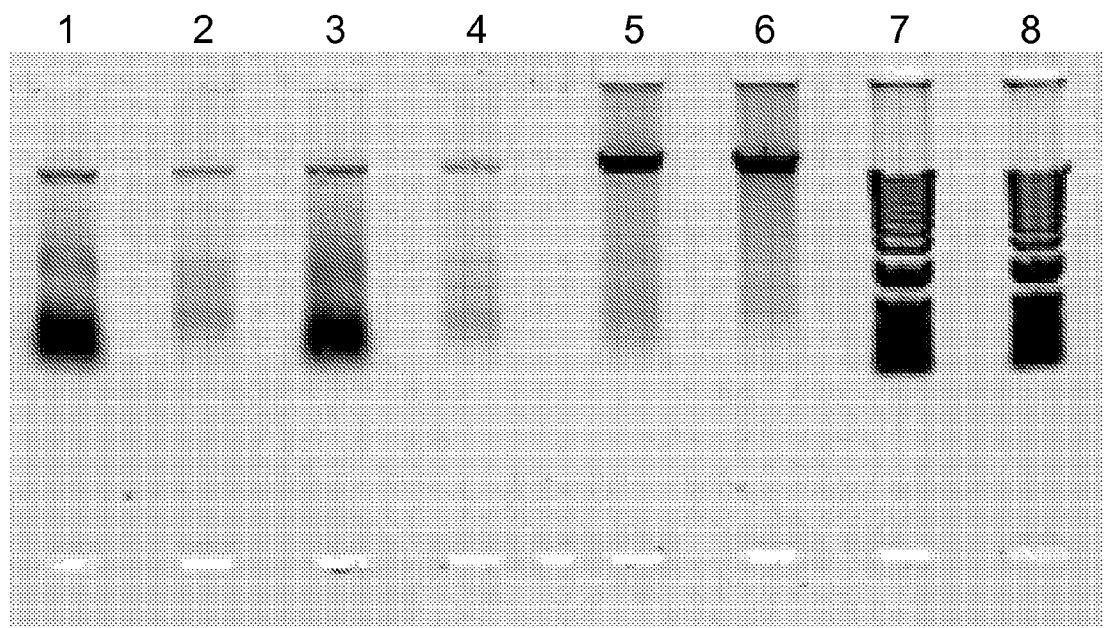
FIG. 2 shows an agarose gel electrophoresis analysis of isolated genomic DNA and RNA, using the method according to one embodiment of the invention.

The quality of the isolated genomic DNA and RNA were examined by agarose gel electrophoresis. FIG. 2 shows the results of two such preparations. Lanes 1, 2 and 5 from one preparation, whiles lanes 3, 4 and 6 from a second preparation. Lanes 7 and 8 shows DNA ladders as a size reference for the samples. It demonstrates that the genomic DNA (lanes 5 and 6) and RNA (lanes 1 and 3) isolated contain predominantly the desired components, with a low level of cross contamination easily removed by treating with a nuclease (lanes 2 and 4 are eluates collected from the intermediate wash step).

The data clearly show that it is possible to accomplish the process. Although it shows a small amount of cross contamination, this can be eliminated by modifying the purification protocol. Alternatively the cross contamination can be removed by treating with enzymes such as RNAse A or DNAse I.

By utilizing this methodology different types of kits can be developed for isolating (1) RNA and protein; (2) DNA and RNA; (3) DNA and protein and (4) DNA, RNA and protein.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for the separation and/or purification of cellular components selected from genomic DNA, RNA and proteins, which method comprising:
   a) generating an aqueous solution containing said cellular components by lysing cells with a lysis solution;
   b) contacting said aqueous solution with an anion exchanger for genomic DNA and RNA to bind to the anion exchanger;
   c) collecting the flow-through which contains unbound proteins;
   d) eluting RNA from said anion exchanger with an RNA elution solution; and
   e) eluting DNA from said anion exchanger with an DNA elution solution;
   wherein said RNA elution solution has a lower salt concentration than said DNA elution solution, and said RNA elution solution has a higher salt concentration than said lysis solution.

2. The method of claim 1, further comprising purifying said proteins collected from step c) by precipitation, gel filtration, affinity chromatography or hydrophobic interaction chromatography (HIC).

3. The method of claim 1, further comprising purifying said genomic DNA eluted from step e) by a desalting step.

4. The method of claim 1, further comprising purifying said RNA eluted from step d) by a desalting step.

5. The method of claim 1, further comprising a wash step after step d), to remove any trace amount of RNA from said anion exchanger.

6. The method of claim 1, wherein said lysis solution has a salt concentration of about 200-500 mM.

7. The method of claim 1, wherein said RNA elution solution has a salt concentration of about 625-750 mM.

8. The method of claim 1, wherein said DNA elution solution has a salt concentration of above about 750 mM.

9. The method of claim 1, wherein the pH of said DNA elution solution is between about pH 9 and about pH 13.

10. The method of claim 1, wherein the pH of said DNA elution solution is between about pH 10 and about pH 12.

11. The method of claim 1, wherein the pH of said DNA elution solution is between about pH 10.5 and about pH 11.6.

12. The method of claim 1, wherein said DNA elution solution comprises potassium carbonate.

13. The method of claim 12, wherein said potassium carbonate is present at a concentration of about 0.1M-2 Molar.

14. The method of claim 1, wherein said anion exchanger is contained within a chromatography column and separation is accomplished by gravity flow, centrifugation, positive pressure or vacuum.

* * * * *